(12) United States Patent
Markussen

(10) Patent No.: US 9,108,002 B2
(45) Date of Patent: Aug. 18, 2015

(54) AUTOMATIC INJECTION DEVICE WITH A TOP RELEASE MECHANISM

(75) Inventor: Tom Hede Markussen, Bagsværd (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 13/326,738

(22) Filed: Dec. 15, 2011

(65) Prior Publication Data

US 2012/0083746 A1    Apr. 5, 2012

Related U.S. Application Data

(63) Continuation of application No. 11/813,435, filed as application No. PCT/DK2006/000032 on Jan. 20, 2006, now Pat. No. 8,096,978.

(60) Provisional application No. 60/647,320, filed on Jan. 26, 2005.

(30) Foreign Application Priority Data

Jan. 21, 2005 (DK) .................................. 2005 00113

(51) Int. Cl.
| | |
|---|---|
| *A61M 5/31* | (2006.01) |
| *A61M 5/315* | (2006.01) |
| *A61M 5/20* | (2006.01) |
| *A61M 5/24* | (2006.01) |

(52) U.S. Cl.
CPC ............ *A61M 5/31525* (2013.01); *A61M 5/20* (2013.01); *A61M 5/31553* (2013.01); *A61M 5/24* (2013.01); *A61M 5/3156* (2013.01); *A61M 5/31583* (2013.01); *A61M 5/31593* (2013.01); *A61M 2005/202* (2013.01)

(58) Field of Classification Search
CPC .......... A61M 5/20; A61M 2005/2026; A61M 2005/2073
USPC .......... 604/134–139, 151–153, 187, 207–211
See application file for complete search history.

(56) References Cited

U.S. PATENT DOCUMENTS

| | | | |
|---|---|---|---|
| 5,104,380 A | * | 4/1992 | Holman et al. ............... 604/117 |
| 5,308,340 A | | 5/1994 | Harris |
| 5,383,865 A | | 1/1995 | Michel |
| 5,496,293 A | | 3/1996 | Huggenberger |
| 5,658,259 A | | 8/1997 | Pearson et al. |
| 5,665,071 A | | 9/1997 | Wyrick |
| 5,728,074 A | | 3/1998 | Castellano et al. |
| 5,820,602 A | | 10/1998 | Kovelman et al. |
| 6,221,046 B1 | | 4/2001 | Burroughs et al. |

(Continued)

FOREIGN PATENT DOCUMENTS

| | | |
|---|---|---|
| EP | 0293958 A1 | 12/1988 |
| EP | 0293958 B | 12/1988 |

(Continued)

*Primary Examiner* — Laura Bouchelle
(74) *Attorney, Agent, or Firm* — Wesley Nicolas

(57) ABSTRACT

The present invention relates to a handheld mechanical injection device by which set doses of a liquid medicament can be injected from a medical reservoir. The medicament is expelled through an injection needle by release of a power reservoir in the device, the power reservoir being fully or partially released by actuation of a user operable release member being positioned at or near an upper end of the injection device, the upper end being that end of the injection device which is opposite the injection needle.

2 Claims, 13 Drawing Sheets

(56) References Cited

U.S. PATENT DOCUMENTS

Figure 1:
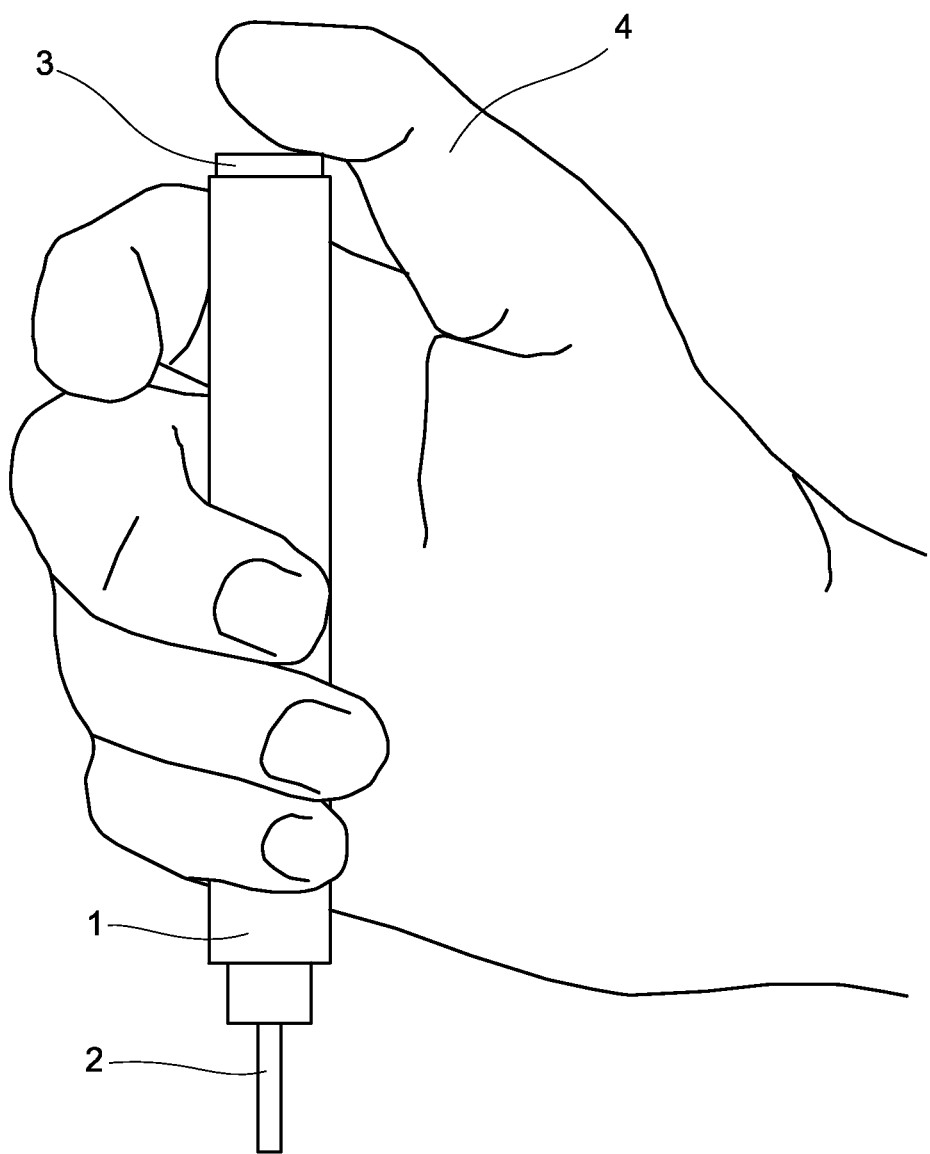

| | | |
|---|---|---|
| 6,277,101 B1 | 8/2001 | Kirchhofer et al. |
| 6,364,860 B1 | 4/2002 | Steck et al. |
| 6,387,078 B1 | 5/2002 | Gillespie, III |
| 6,620,137 B2 | 9/2003 | Kirchhofer et al. |
| 6,663,602 B2 | 12/2003 | Moller |
| 6,673,049 B2 | 1/2004 | Hommann et al. |
| 6,699,224 B2 | 3/2004 | Kirchhofer et al. |
| 6,743,203 B1 | 6/2004 | Pickhard |
| 7,241,278 B2 | 7/2007 | Moller |
| 7,445,613 B2 | 11/2008 | Hommann |
| 7,500,966 B2 | 3/2009 | Hommann |
| 8,357,120 B2 | 1/2013 | Moller et al. |
| 8,684,969 B2 | 4/2014 | Moller et al. |
| 2002/0095120 A1 | 7/2002 | Larsen et al. |
| 2004/0019326 A1 | 1/2004 | Gilbert et al. |

FOREIGN PATENT DOCUMENTS

| | | |
|---|---|---|
| EP | 0554996 A1 | 8/1993 |
| EP | 0554996 B | 8/1993 |
| EP | 0516473 A1 | 2/1996 |
| EP | 1294418 | 9/2005 |
| JP | 2071758 | 3/1990 |
| JP | 2002-502296 A | 1/2002 |
| RU | 2091087 | 9/1997 |
| RU | 2212254 | 9/2003 |
| SU | 1528330 A3 | 12/1989 |
| WO | 88/08725 A1 | 11/1988 |
| WO | 94/13343 A1 | 6/1994 |
| WO | 01/41838 A1 | 6/2001 |
| WO | 0195959 | 12/2001 |
| WO | 03/097133 A1 | 11/2003 |
| WO | 2006/045528 A1 | 5/2006 |

* cited by examiner

AUTOMATIC INJECTION DEVICE WITH A TOP RELEASE MECHANISM

CROSS-REFERENCE TO RELATED APPLICATIONS

This application is a continuation of U.S. patent application Ser. No. 11/813,435 filed Jun. 2, 2008 (U.S. Pat. No. 8,096,978, issued Jan. 17, 2012) which is a 35 U.S.C. §371 national stage application of International Patent Application PCT/DK2006/000032 (published as WO 2006/076921), filed Jan. 20, 2006, which claimed priority of Danish Patent Application PA 2005 00113, filed Jan. 21, 2005; this application further claims priority under 35 U.S.C. §119 of U.S. Provisional Application 60/647,320, filed Jan. 26, 2005.

The present invention relates to an automatic and handheld mechanical injection device where an injection of a set dose of medicament is initiated by actuating a release member being arranged at or near the top of the injection device.

BACKGROUND OF THE INVENTION

Automatic injection devices have previously been disclosed in the patent literature. Automatic injection devices contain some sort of power reservoir where electrical or mechanical energy can be accumulated. The accumulated energy is easily released by actuating a release mechanism whereby the accumulated energy assists the user in injecting a set dose of medicine and/or assisting needle insertion.

For example, EP 0 516 473 A1 discloses an injection device having a needle which, when the device is operated, is first caused to project, then liquid is forced out through it, and finally the needle is automatically retracted. The needle extends forwardly from a capsule that can slide longitudinally within a barrel-like body, a relatively weak spring normally maintaining the capsule and needle retracted. A more powerful spring acts oppositely on a plunger which, when released, shoots the capsule forward by acting on the liquid therein, and then forces the liquid out through the projecting needle. At the end of the forward stroke the plunger and capsule are decoupled and the weak spring returns the exhausted capsule and its needle to the retracted position. The spring acting on the plunger can be released by a release button positioned on the outer surface of the injection device.

In WO 01/41838 discloses a handheld injection device by which set doses of a liquid medicament can be injected from a medical reservoir, such as cylinder ampoule, by release of a power reservoir in the device. The power reservoir can either be an electric battery by which a motor can be energized to press out a set dose of medicine, or a strained spring maintained in its strained position by a detent which spring when released can press out a set dose of medicine. When the power reservoir is released, the liquid medicine will be pressed out from the cylinder ampoule through an injection needle mounted on the cylinder ampoule or on the injection device carrying the cylinder ampoule. The power reservoir is released fully or partially by activating a release button, such as an electric switch, located on the housing of the injection device and in the distal half of the length of the injection device. By making at least a part of the distal third of the injection device of an ergonomic shaped cross section, the user can grip the injection device as a pencil is gripped by a thumb, an index finger and a long finger.

In both EP 0 516 473 A1 and WO 01/41838 the release buttons are positioned on an outer surface of the injection devices. In EP 0 516 473 A1 the release button is position on the outer side of the cylindrical body, whereas in WO 01/41838 the release button is positioned close to the injection needle of the injection device. However, it may be advantageous to position the release button or mechanism so that the injection device can be activated by providing a force to the upper region of the injection device—preferably to a release button or mechanism arranged axially with the injection device.

It is an object of the present invention to provide an automatic and handheld mechanical injection device having a combined release member and dose setting member.

It is a further object of the present invention to provide an automatic and handheld mechanical injection device where an injection of a set dose can be initiated using the thumb or the index finger of the hand handling the injection device by providing an axial force to an upper region of the injection device.

It is a still further object of the present invention to provide an automatic and handheld mechanical injection device having an exterior design very similar to conventional manual injection devices.

SUMMARY OF THE INVENTION

The above-mentioned objects are complied with by providing, in a first aspect, a handheld injection device by which set doses of a liquid medicament can be injected from a medical reservoir through an injection needle by release of a power reservoir in the device, the power reservoir being adapted to be fully or partially released by actuation of a user operable release member positioned at or near an upper end of the injection device, the upper end being that end of the injection device which is opposite the injection needle, the power reservoir being adapted to be powered by rotation of a rotatably mounted dose setting member.

The amount of power provided to the power reservoir may depend on the angle of rotation of the dose setting member. Thus, a rather limited rotation of the dose setting member provides a relatively small amount energy to the power reservoir, whereas a large rotation of the dose setting member provides a relatively large amount of energy to the power reservoir.

The release member may be positioned less than one fifth or one sixth of the length of the injection device from the upper end. Alternatively, the release member may be axially arranged relative to the injection device so that the release member forms a push button like release member on the top of the injection device.

The release member may be operatively connected to a dose setting member of the injection device in that the release member may engage the dose setting member via a key/keyway connection when the dose setting member is in a dose setting position. The release member may be released from the key/keyway connection with the dose setting member when the dose setting member is in a dose injecting position. With this arrangement, the handheld injection device has no rotating exterior parts or elements.

The power reservoir may be a resilient member, such as a torsion spring or a linear spring, the resilient member being, when released, adapted to press out a set dose of medicine from the medical reservoir through the injection needle. The release member may be operatively connected to a release mechanism adapted to release the resilient member when said release member is actuated. The release member may have a shape which is ergonomic shaped to be activated by a thumb or an index finger of the user.

The medical reservoir may be a cylindrical ampoule comprising a first and a second end of which the first end is closed by a pierceable membrane which may be pierced by a first end of the injection needle when this needle is mounted on the device. The other end of the injection needle may be sharp so as to be able to pierce the skin at the position where an injection is to be made. The second end of the ampoule may be closed by a piston which may be forced into the ampoule so as to expel medicament through the needle.

The handheld injection device may further comprise a rotatably arranged drive member being adapted to at least partly engage with at least part of a drive track of an associated piston rod, the drive member being adapted to be positioned in a first axial position when the dose setting member is in a dose setting position, the drive member further being adapted to be positioned in a second axial position when the dose setting member is in a dose injection position, the drive member being adapted to release energy accumulated in the power reservoir when the drive member is in its second axial position.

The drive member may be adapted to rotate the associated piston rod upon releasing the accumulated energy in the power reservoir. However, in its first axial position, the drive member is prevented from rotating because the drive member engages at least part of a housing of the injection device. The injection device may further comprise a resilient member, such as a linear spring, for biasing the drive member in a direction towards the dose setting member. The linear spring operatively connects the drive member and the housing.

The dose setting member may be adapted to be moved a distance along an axial direction of the injection device so as to move the drive member between the first and second axial positions. The drive member may be adapted to be moved from the first to the second axial position by applying a force to the dose setting member, the force being applied along the axial direction of the injection device.

The injection device may, as already mentioned, further comprise a push button axially arranged with the dose setting member, the push button being adapted to engage with the dose setting member when the dose setting member is in its dose setting position, and disengage from the dose setting member when the dose setting member is in its dose injection position. By disengage is meant that the push button and the dose setting member are mutually rotatable when this disengaged state is reached. The injection device may further comprise a resilient member, such as a linear spring, for axially biasing the push button in a direction away from the drive member.

The handheld injection device may further comprise a rotatably mounted display member adapted to display the dose to be ejected from the injection device in accordance with a setting of the dose setting member, the rotatably mounted display member being rotatable over an angle corresponding to at least one revolution of the display member. The display member may comprise a dose indicator barrel having numerals arranged along a substantially helical path on an outer surface thereof. Alternatively or in addition, the display member may comprise a counting device having two or more display wheels having numerals arranged on an outer surface thereof.

The handheld injection device may further comprise the associated the piston rod, the piston rod having a threaded outer surface with the drive track arranged in a longitudinal direction of the outer surface of the piston rod. The drive member may be operatively connected to the dose setting member via a ratchet.

The power reservoir may be arranged between the housing and the dose setting member in such a way that when the dose setting member is rotated, energy is accumulated in the power reservoir. The power reservoir may comprise a torsion spring formed as a helical spring extending coaxially with the associated piston rod.

It is to be noted that the interaction between the drive member, the piston rod and the housing may be implemented in various ways. Above, the piston rod has a threaded outer surface and a drive track arranged in the longitudinal direction of the rod. A key arranged on the drive member engages the drive track of the rod and the forward movement of the rod relative to the housing is caused by the threaded outer portion of the rod which meshes with a corresponding threaded portion of the housing. Alternatively, the threaded outer surface of the rod may mesh with a corresponding threaded portion of the drive member whereas the drive track arranged in the longitudinal direction of the rod engages with a key fixedly arranged relative to the housing.

BRIEF DESCRIPTION OF THE INVENTION

Figure 2:
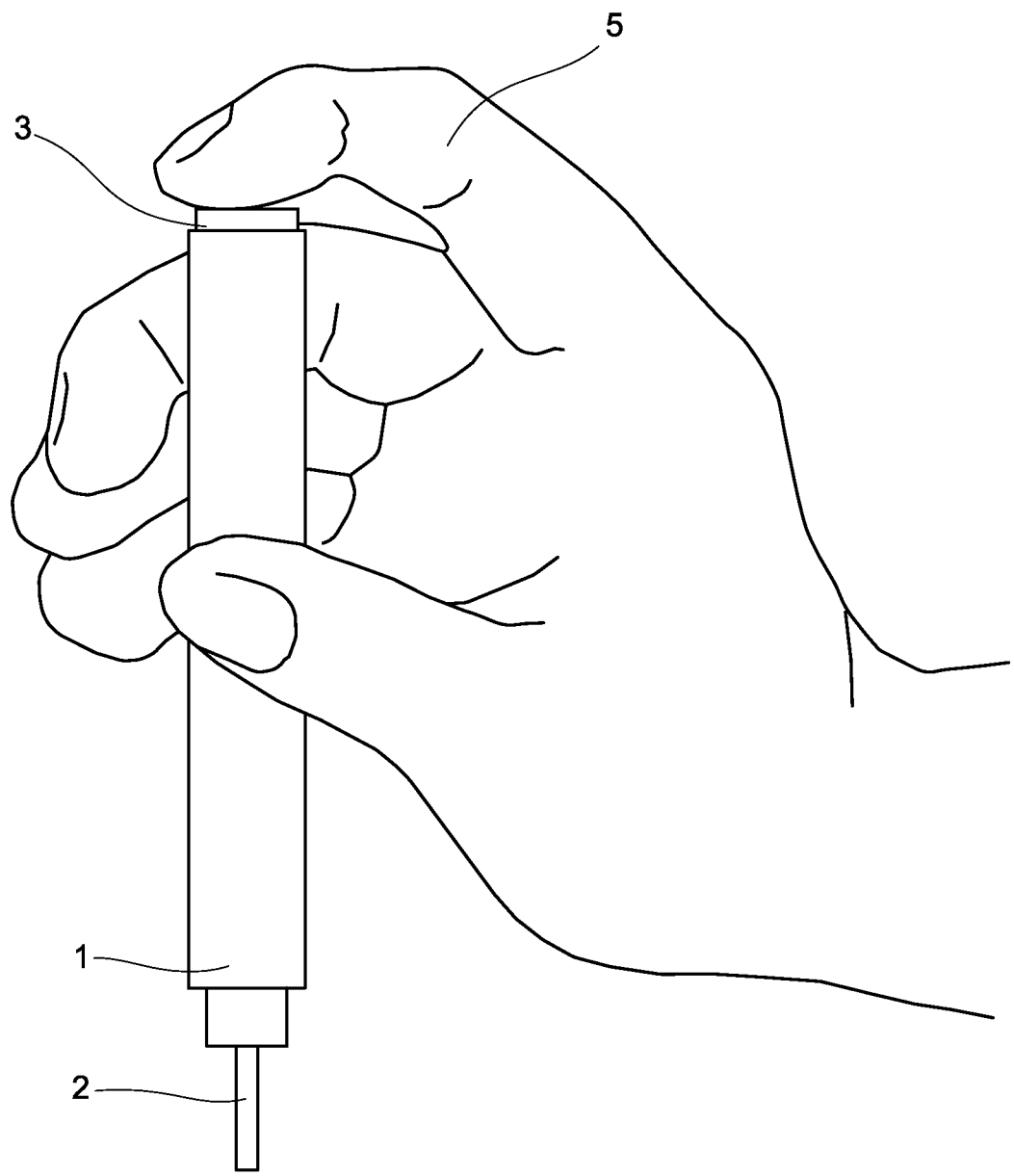
Figure 3:
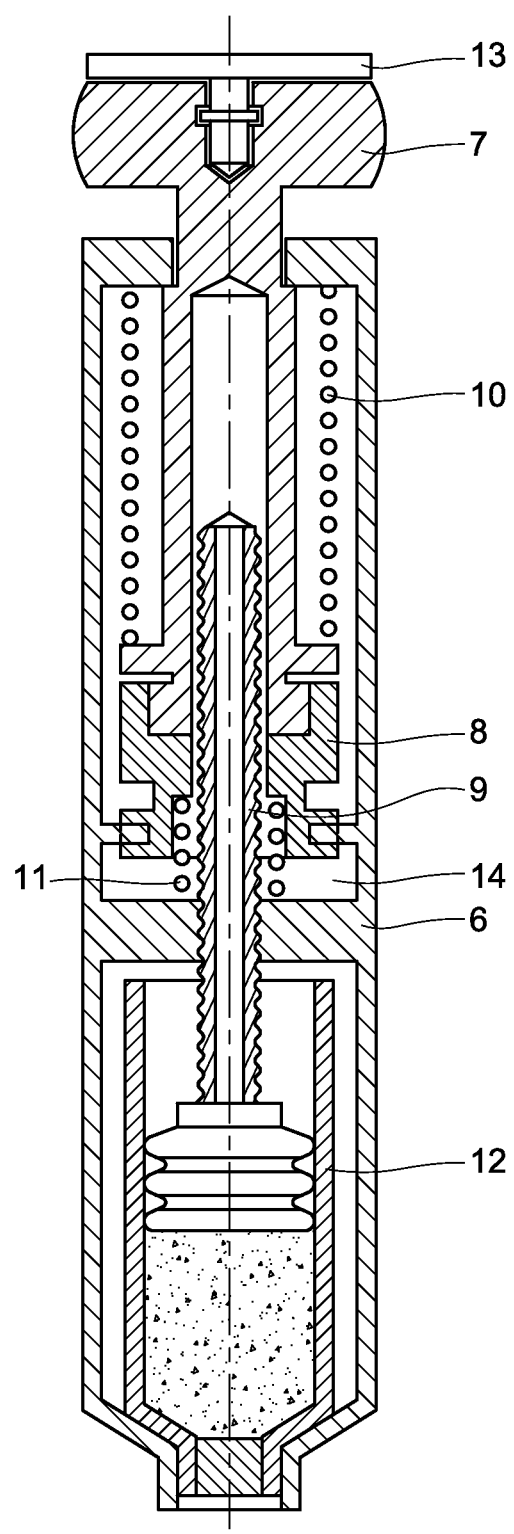
Figure 4:
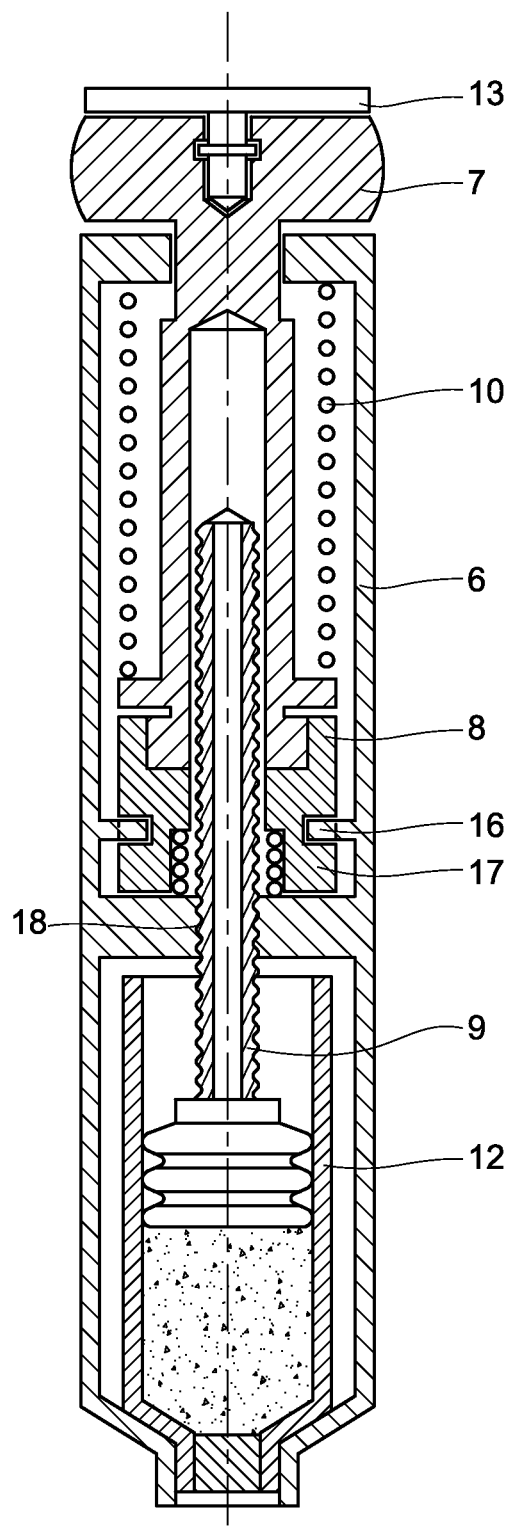
Figure 5:
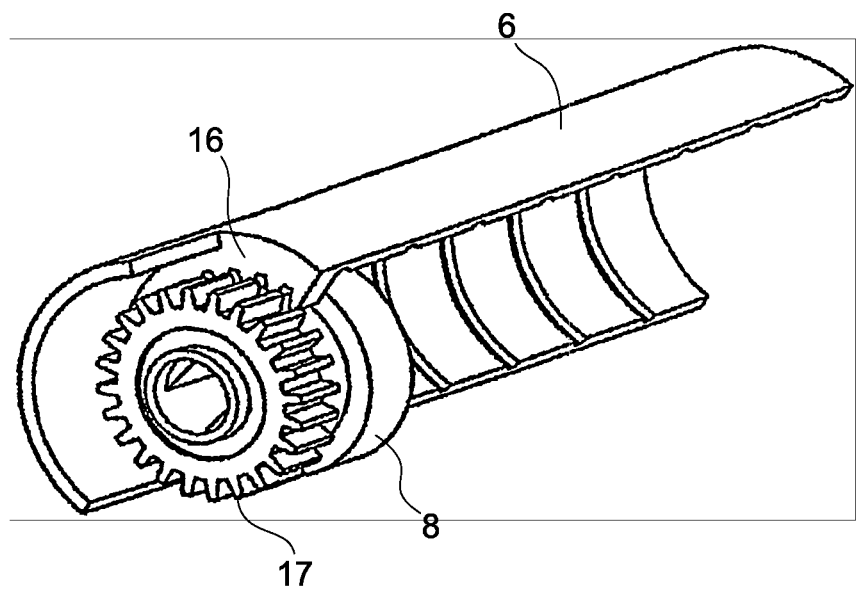
Figure 6:
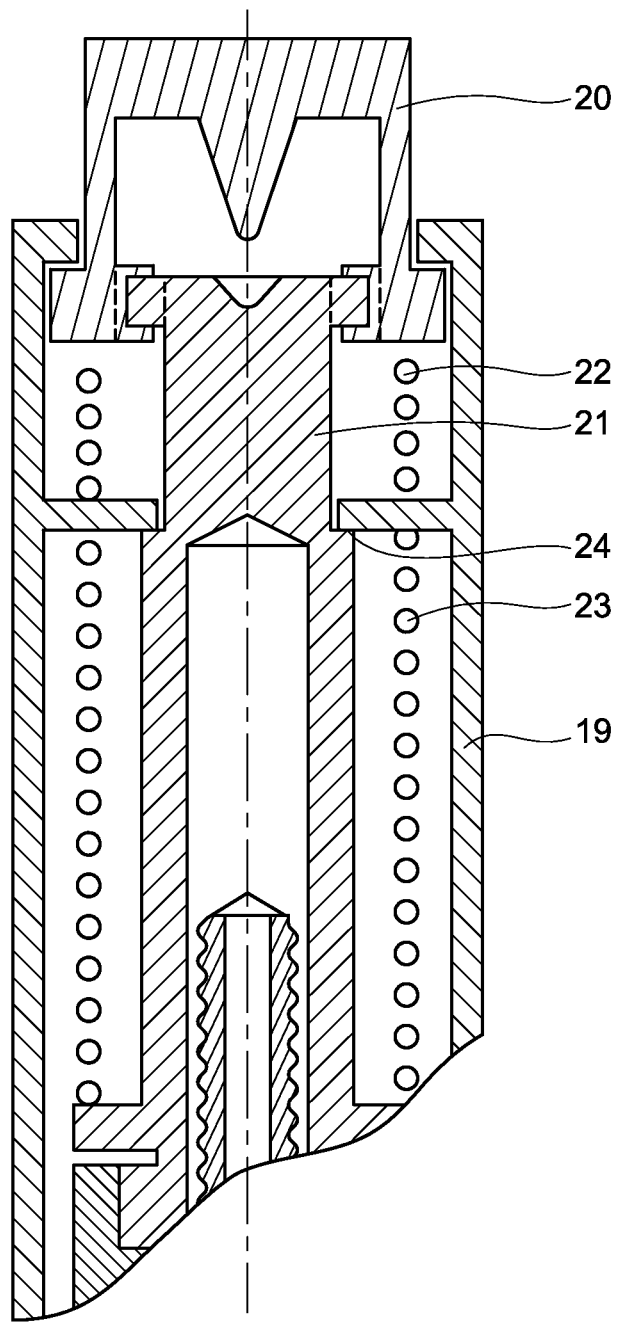
Figure 7:
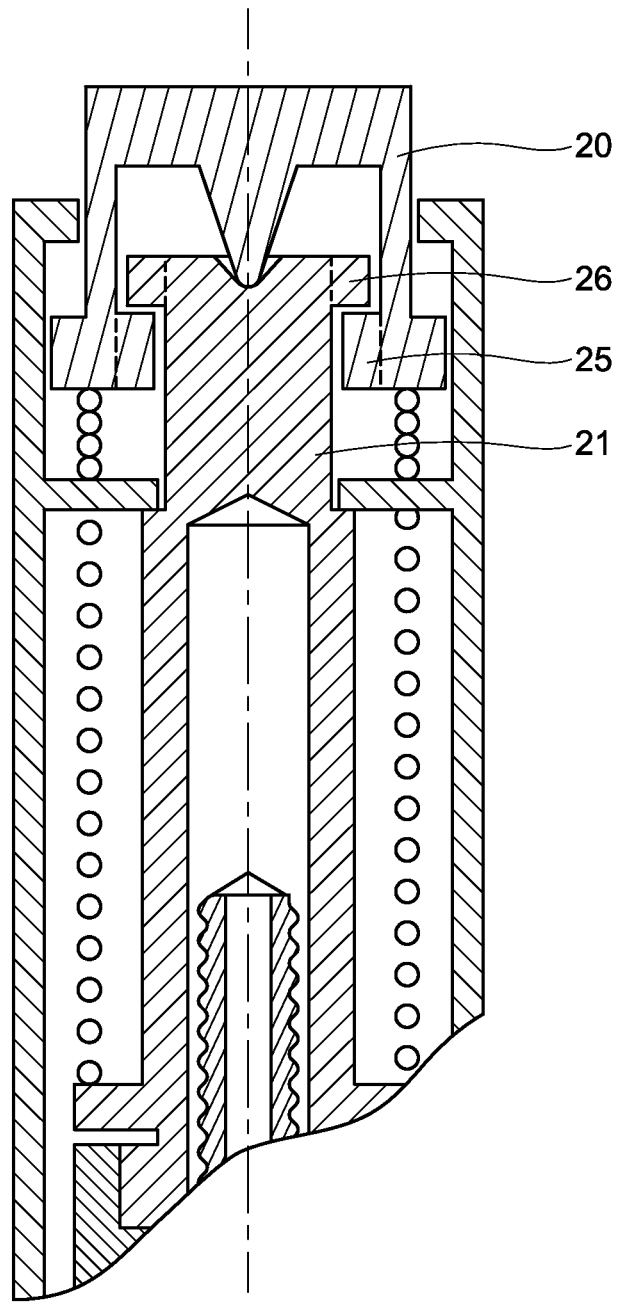
Figure 8:
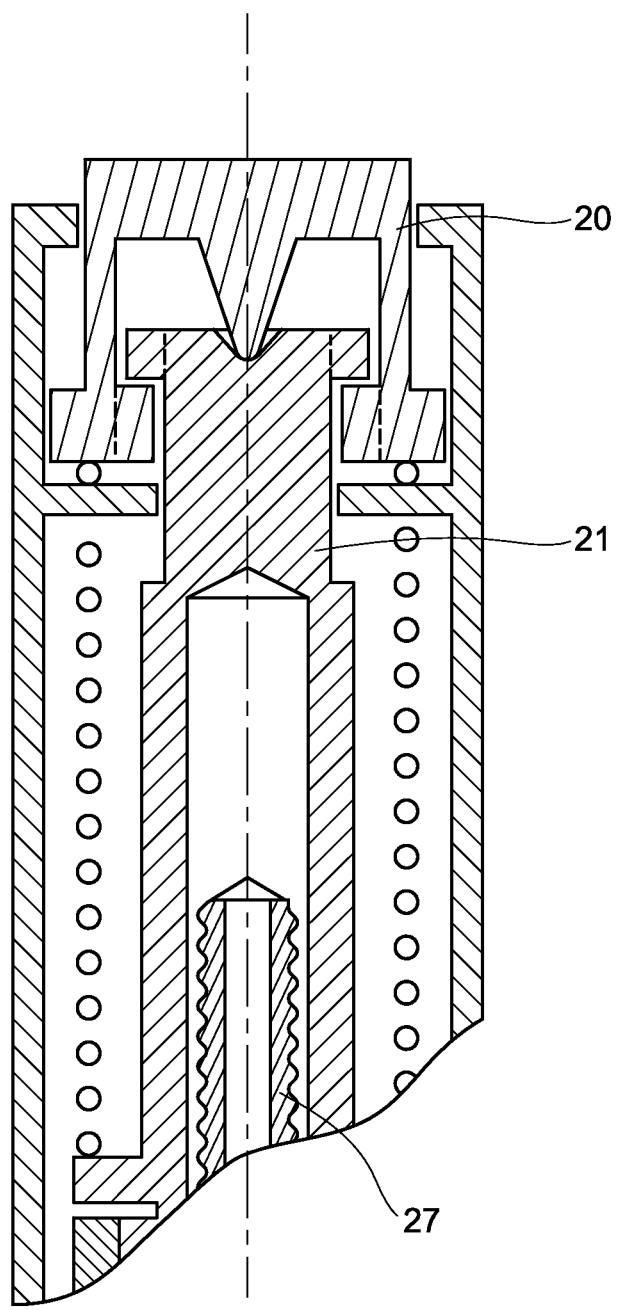
Figure 9:
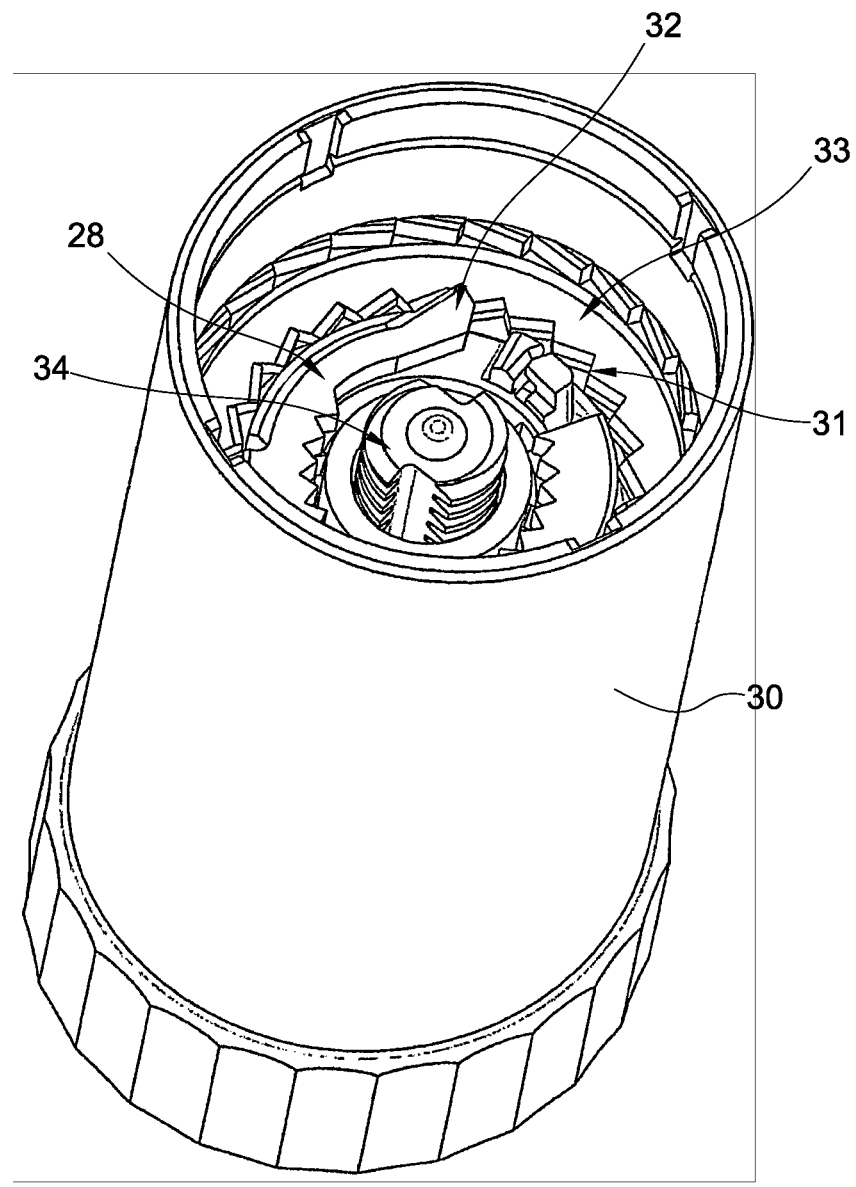
Figure 10:
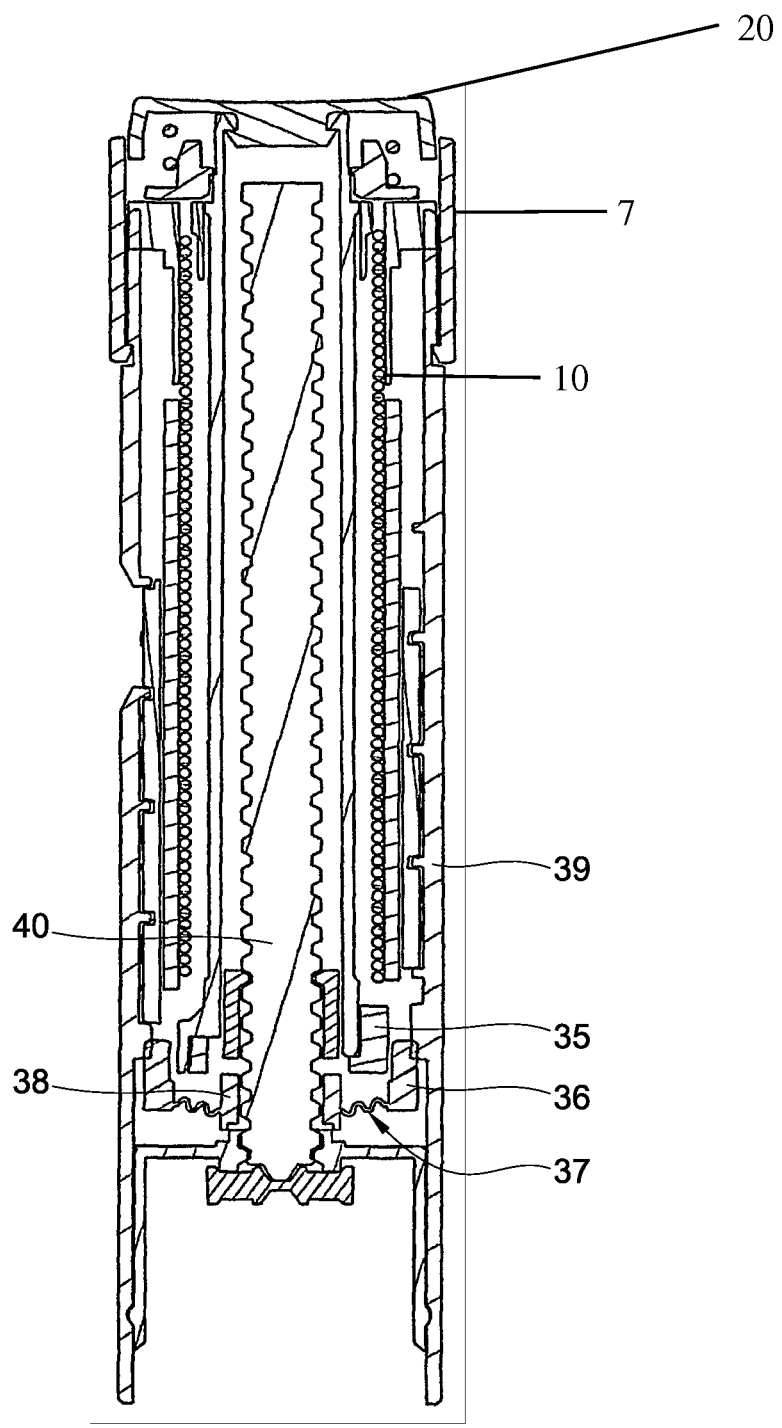
Figure 11:
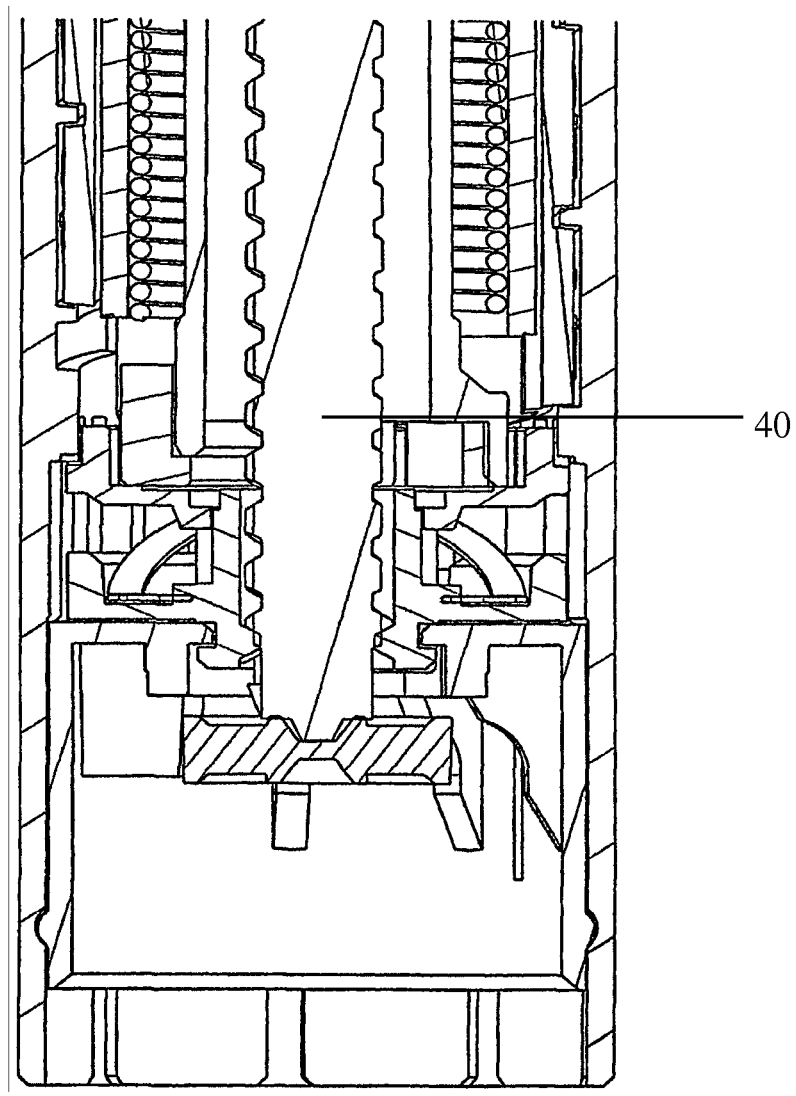
Figure 12:
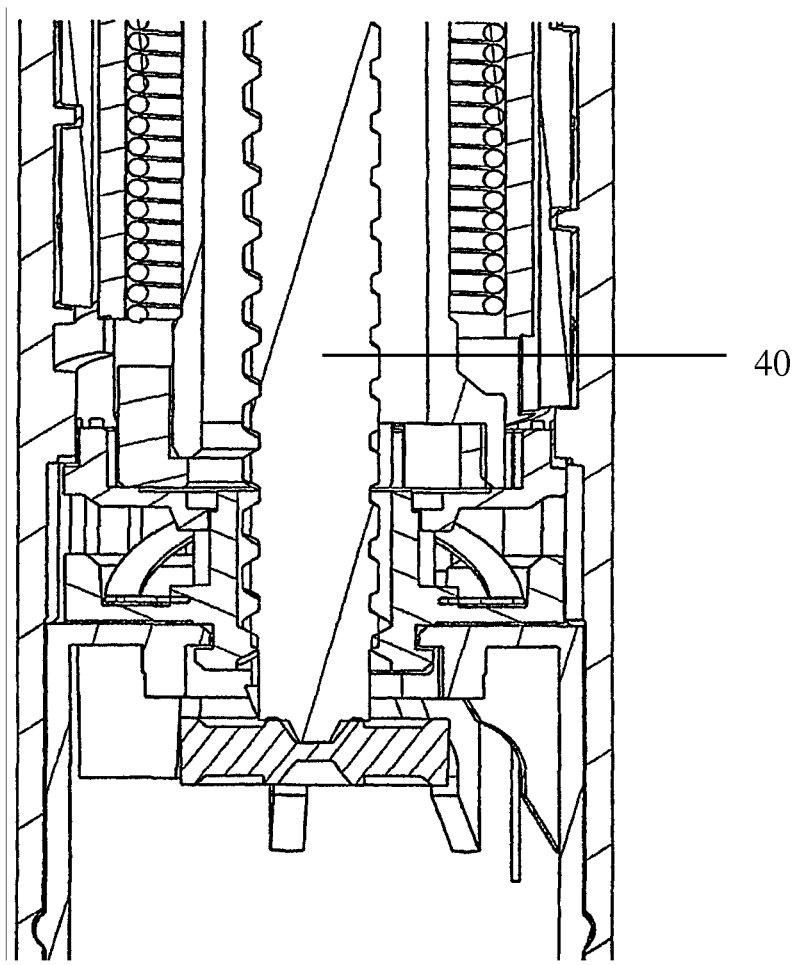
Figure 13:
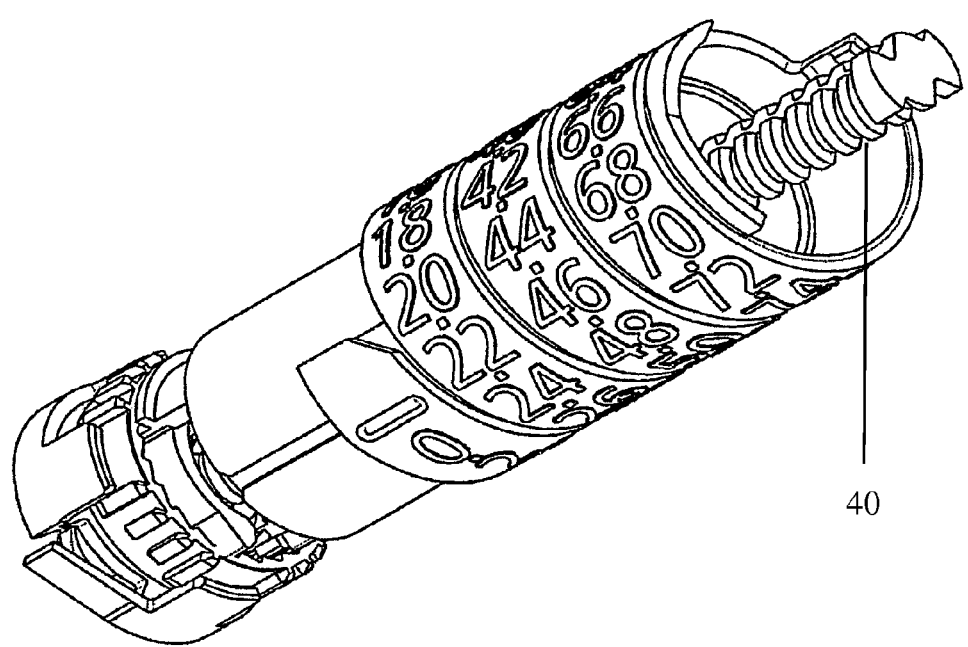

The present invention will now be explained in further details with reference to the accompanying figures wherein FIG. 1 shows an injection device according to the present invention where the release button arranged at the top of the device is activated by the thumb of the user, FIG. 2 shows an injection device according to the present invention where the release button arranged at the top of the device is activated by the index finger of the user, FIG. 3 shows an injection device according to the present invention where the release button is arranged on the top surface of the dose setting member, and where the drive member is in its locked position (dial position of dose setting member), FIG. 4 shows an injection device according to the present invention where the release button is arranged on the top surface of the dose setting member, and where the drive member is in its released position (dosing position of dose setting member), FIG. 5 shows an expanded view of the drive member in its released position, FIG. 6 shows an expanded view of the release member in its locked position with the dose setting member, FIG. 7 shows an expanded view of the release member in its released position with the dose setting member, FIG. 8 shows an expanded view of the release member in a further released position where the dose setting member is allowed to rotate, FIG. 9 shows one way of implementing the release mechanism for releasing the energized power reservoir, FIG. 10 shows another way of implementing the release mechanism for releasing the energized power reservoir, FIG. 11 shows a third way of implementing the release mechanism for releasing the energized power reservoir, FIG. 12 shows a fourth way of implementing the release mechanism for releasing the energized power reservoir, and FIG. 13 shows a fifth way of implementing the release mechanism for releasing the energized power reservoir.

While the invention is susceptible to various modifications and alternative forms, specific embodiments have been shown by way of example in the drawings and will be described in detail herein. It should be understood, however, that the invention is not intended to be limited to the particular forms disclosed. Rather, the invention is to cover all modifications, equivalents, and alternatives falling within the spirit and scope of the invention as defined by the appended claims.

DETAILED DESCRIPTION OF THE INVENTION

FIGS. 1 and 2 show the present invention in its most general aspect. In FIG. 1 a handheld injection device 1 is shown.

The injection device has an injection needle 2 fastened to one of its ends, whereas a release button 3 is arranged at the opposite end of the injection device. When the release button 3 is actuated by provided a force to it along the axial direction of the device energy is released from an internal power reservoir whereby a set dose of medicine is injected from the injection device. In FIG. 1 the release button is actuated by the thumb 4 of the user, whereas in FIG. 2 the release button is actuated by the index finger 5 of the user.

The medicine to be injected is contained in a medical reservoir typically formed as a cylindrical ampoule.

The energy released when the release button 3 is mechanical energy. The power reservoir can be a resilient member, such as a torsion spring, the resilient member being, when released, adapted to press out a set dose of medicine from the medical reservoir through the injection needle. The release button is operatively connected to some sort of release mechanism adapted to release the resilient member when the release button is actuated.

FIG. 3 shows a cross-sectional view of one embodiment of the present invention. The injection device shown in FIG. 3 comprises a housing 6, a dose setting member 7, a drive member 8, a piston rod 9, a torsion spring 10, a biasing spring 11, a cylindrical ampoule 12 and a release member 13. FIG. 3 shows the injection device in a state where the dose setting member 7 is in its dose setting position.

A dose is set by rotating the dose setting member 7 a certain angle or a certain number of turns. By rotating the dose setting member 7 the torsion spring 10 is strained because the two ends of the torsion spring 10 are fixed to the housing 6 and to the dose setting member 7, respectively. The dose setting member 7 is operatively connected to the drive member 8 via a ratchet (not shown). This ratchet prevents that the dose setting member 7 returns to its initial position upon straining the torsion spring 10. Since the drive member 8 engages the housing 6 via a key/keyway connection or a gear wheel, the drive member 8 is not allowed to rotate relative to the housing 6 as long as the dose setting member 7 is in its dose setting position as illustrated in FIG. 3. In order to keep the dose setting member 7 and the drive member 8 in the dose setting position, the drive member 8 and the dose setting member 7 is biased in a direction towards the top end of the injection device. This biasing is provided by a spring element, such as a linear spring 11, arranged between the drive member 8 and part of the housing 6. Thus, in order to release the drive member 8 from its engagement with the housing 6, a force needs to be provided in order move the dose setting member 7 and the drive member 8 towards the medicine ampoule 12. A miner cavity 14 ensures that this forward movement of the dose setting member 7 and the drive member 8 can be performed. Similarly, since the dose setting member 7 and the piston rod 9 engage via a key connection the drive member 8 is allowed to move axially relative to the piston rod 9.

The drive member 8 has been released from its engagement with the housing 6 in FIG. 4. In order to achieve this releasing a force, indicated by arrow 15, has been provided to the release member 13 whereby the release member 13, the dose member 7 and the drive member 8 have all been moved a distance towards the medicine ampoule 12. The force indicated by arrow 15 would normally be provided by the thumb or the index finger of the user.

As seen in FIG. 4 the engaging region 16 of the housing is now separated from the engaging region 17 of the drive member 8. This disengagement allows that the strained torsion spring 10 can release its energy to the dose setting member 7. The dose setting member 7 and the drive member 8 are fixedly related via the intermediate ratchet (not shown). Thus, when a disengagement between engaging regions 16 and 17 has been established, the dose setting member 7 and the drive member 9 will rotate until the torsion spring 10 reaches an unstrained state. Since the drive member 8 and the piston rod 9 is connected via a key connection the rotation of the dose setting member 7 and the drive member 8 will cause the piston rod 9 to rotate as well. The piston rod 9 has an outer threaded surface which engages with a corresponding threaded portion 18 of the housing whereby the piston rod 9, upon rotation thereof, will perform a translational movement along the axial direction of the injection device in the direction of the ampoule 12.

Thus, the force provided to the release member 13 will release accumulated energy in the torsion spring. This energy is converted to a translational movement of the piston rod towards the ampoule whereby a set dose of medicine can be injected from the injection device.

FIG. 5 shows a cut half illustration of the housing 6 of the injection device. As seen, the drive member 8 comprises an engagement region/part 17 formed as gear wheel. Similarly, the housing 6 comprises a corresponding engagement region/part 16 adapted to receive and engage with the teeth of the gear wheel 17.

FIG. 6 shows another embodiment of the present invention. In contrast to the embodiment shown in FIGS. 3-5 the embodiment shown in FIG. 6 contains no rotating exterior parts or elements. All rotating parts or elements are positioned inside the housing 19. FIG. 6 shows a release member 20 (formed as a push button) which is mechanically biased towards the end of the injection device by spring element 22. The release member 20 and dose setting member 21 are forced into engagement as long as the dose setting member 21 is in its dose setting position. The dose setting member 21 is mechanically biased towards the same end of the injection device as the release member 20 due to a spring element (shown as spring element 11 in FIG. 3) acting on the drive member (shown as drive member 8 in FIG. 3) which again acts on dose setting member 21. As seen in FIG. 6 the dose setting member 21 is biased against a mechanical stop 24 where a shoulder formed in the dose setting member 21 abuts a part of the housing 19.

In FIG. 7 an intermediate stage is illustrated. Here the release member 20 has been pushed an axial distance sufficient to release the release member 20 from the dose setting member 21. Note that the engagement region 25 and 26 are disengaged, but since the shoulder of the dose setting member still abuts the housing part no axial movement of the dose setting member 21 has been achieved at this stage. Thus, the dose setting member 21 is prevented from rotating since the drive member (not shown) is still engaging the housing.

In FIG. 8 the dose setting member 21 has been moved an axial distance towards the ampoule (not shown) whereby the dose setting member is allowed to rotate freely causing the piston rod 27 push a set dose of medicine out of the ampoule (not shown). Note that the release member 20 and the dose setting member 21 are disengaged in FIG. 8. This means that the release member 20 is not rotating relative to the housing during injection of a set dose. Then the set dose has been injected the user removes his thumb or index finger from the release member whereby the release member and the dose setting member return to their respective positions as illustrated in FIG. 6, but now with the spring element 23 being in a relaxed state.

In case the user wants to set a new dose, the user rotates the release member which engages the dose setting member whereby the new dose can be set. Injecting the set dose is achieved by following the steps illustrated in FIGS. 7 and 8.

FIGS. 9-13 show various embodiments of release mechanisms for releasing the energized power reservoir.

In FIG. 9 a torsion spring (not shown) is energized by rotating a ratchet 28 which is operatively connected to the housing 30 of the injection device when the dose to be injected is being set. In the dose setting position the ratchet 28 is operatively connected with housing part 31 via ratchet arm 32. Energy accumulated in the torsion spring is released by displacing the ratchet 28 axially whereby it is released from its connection with housing part 31 in that the ratchet arm 32 is moved into housing part 33 whereby the piston rod 34 is allowed to rotate thereby expelling a set dose of medicament.

In the embodiment depicted in FIG. 9 a dose indicator barrel (not shown) moves in the direction away from the push-button (not shown) during setting of a dose. Obviously, the dose indicator barrel may be adapted to move in the opposite direction during setting of a dose, i.e. towards the push-button.

In the embodiment depicted in FIG. 10 the ratchet 35 is only in indirect operation with the housing 39. The drive member of the embodiment depicted in FIG. 10 is constituted by three part—one part 36 being adapted to corporate with the housing 39, another part 38 being adapted to drive the piston rod 40 and a flexible member 37 connecting parts 36 and 38. The flexible member 37 is flexible in the axial direction but establishes a substantially stiff connection between parts 36 and 38 when these parts are rotated relative to each other. Thus, the flexible member 37 ensures that parts 36 and 38 are not rotatably arranged relative to each other. Thus, when the ratchet 35 is moved towards the needle end of the injection device the part 36 is disconnected from the housing 39 whereby parts 36, 37 and 38 are allowed to rotate thereby rotating the piston rod 40. The rotating piston rod 40 causes a set dose of medicament to be expelled from the injection device.

The embodiment depicted in FIG. 11 is similar to the embodiment in FIG. 9 except that the piston rod is moved forward by having guiding tracks arranged in the housing (instead of in the drive member) and a threaded engagement between piston rod and the drive member (instead of a threaded engagement between piston rod and housing).

FIGS. 12 and 13 show other release mechanisms between ratchet, drive member and housing.

The invention claimed is:

1. A handheld injection device, comprising:
   a rotatable dose setting member that is rotatable about a longitudinal axis of a housing of the injection device;
   a power reservoir, comprising a torsion spring for storing energy to expel a dose from the injection device;
   a piston rod;
   a release member, located at the most proximal portion of the device, opposite an end of the device wherein a needle may be mounted;
   the injection device, further comprising a rotatably arranged multi-component driver (36, 37, 38) having at least a part (38) that at least partly engages with at least part of a drive track of an associated piston rod, and a further part (36) being axially movable into a position disconnected from the housing thus releasing energy accumulated in the power reservoir, the further part (36) being axially movable by the user applying a force onto a generally planar surface of the release member, wherein the generally planar surface is generally perpendicular to a longitudinal direction of the piston rod in the device.

2. An injection device comprising:
   a housing;
   a drive member;
   a piston rod having a longitudinal direction;
   a torsion spring for storing energy to drive a dose from the injection device;
   a drive mechanism converting relative rotational motion into axial movement of the piston rod;
   a release button located at the most proximal end of the device, opposite an end of the device wherein a needle may be mounted, the release button having a generally planar surface that is generally perpendicular to the longitudinal direction of the piston rod.

* * * * *